United States Patent [19]
Goldman

[11] Patent Number: 5,449,002
[45] Date of Patent: Sep. 12, 1995

[54] CAPACITIVE BIOFEEDBACK SENSOR WITH RESILIENT POLYURETHANE DIELECTRIC FOR REHABILITATION

[76] Inventor: Robert J. Goldman, 3607 Baring St., Philadelphia, Pa. 19104

[21] Appl. No.: 908,121
[22] Filed: Jul. 1, 1992
[51] Int. Cl.⁶ .......................................... A61B 5/103
[52] U.S. Cl. ................... 128/779; 128/782; 128/774; 340/573; 361/291
[58] Field of Search ............... 128/774, 779, 782, 905; 73/172; 340/573; 361/290, 291

[56] References Cited

U.S. PATENT DOCUMENTS

| | | | |
|---|---|---|---|
| 3,702,999 | 11/1972 | Gradisar | 340/272 |
| 3,791,375 | 2/1974 | Pfeiffer . | |
| 3,974,491 | 8/1976 | Sipe | 340/272 |
| 4,426,884 | 1/1984 | Polchaninoff | 73/172 |
| 4,503,705 | 3/1985 | Polchaninoff | 73/172 |
| 4,617,525 | 10/1986 | Lloyd | 340/573 |
| 4,647,918 | 3/1987 | Goforth | 340/573 |
| 4,745,930 | 5/1988 | Confer | 128/779 |
| 4,852,443 | 8/1989 | Duncan et al. | 84/1.04 |
| 5,060,527 | 10/1991 | Burgess | 73/862.68 |
| 5,081,447 | 1/1992 | Echols | 340/573 |
| 5,209,240 | 5/1993 | Jain et al. | 128/779 |
| 5,323,650 | 6/1994 | Fullen et al. | 73/172 |

FOREIGN PATENT DOCUMENTS

| | | | |
|---|---|---|---|
| 0415036 | 3/1991 | European Pat. Off. | 128/779 |
| 2675370 | 10/1992 | France | 128/779 |
| 3812287 | 10/1989 | Germany | 128/779 |
| 4135940 | 5/1993 | Germany | 128/779 |

OTHER PUBLICATIONS

Endicott et al "Leg Load . . . handicapped" Medical and Biological Engineering, May 1974 pp. 318-320.
"The Limb Load Monitor: An Augmented Sensory Feedback Device", R. Craike et al., Devices and Systems for the Disabled, Apr. 29 & 30, 1975, Sponsored by Krusen Center for Research & Engineering at Moss Rehabilitation Hospital pp. 18-24.
"Capacitive Transducer for Continuous Measurement of Vertical Foot Force", S. Miyazaki, A. Ishida; Med. & Biolog. Eng & Computing, 1984, 22, pp. 309 to 316.
Proceedings of the Ninth Annual Conference of the IEEE/Engineering in Medicine and Biology Society, The Boston Park Plaza Hotel, Boston, Mass. Nov. 13-16, 1987. "Pressure Monitoring Under Insensate Feet" Maale, et al.
RESNA, 13th Annual Conference, 1990, pp. 201, 202 W. Hyman et al.
Foot & Ankle/ vol. 9, No. 3/Dec., 1988, "Objective Evaluation of Insert Material for Diabetic and Athletic Footwear", J. W. Brodsky et al. pp. 111-116.
Sensors, May 1991, pp. 21-25 Tecscan Inc.
E.Q., Inc. 600 Galahad Road, Plymouth Meeting, Pa., 19462, "Engineering tools for rehabilitation therapy" Date unknown.
F-SCAN ®: "Introducing F-SCAN ®," Tekscan, Inc. (Date unknown).
Biomechanical Studies: "A Method of Measuring Foot Pressures Using A High Resolution, Computerized Insole Sensor: The Effect of Heel Wedges on Plantar Pressure Distribution and Center of Force", Nicholar M. Rose, M.D., Lawrence A. Feiwell, M.D., Andrea Cracchiolo II, M.D. p. 10, date unknown.
Combined Meeting of the the Orthopaedic Research Societies of USA, Japan & Canada: "A New Flexbile Sensor to Evaluate Dynamic In-Shoe Plantar Pressure During Gait and Its Use to Measure the Effect of Shoe Accommodation Devices In Severe Metatarsalgia," B. J. Ambrey, M.D., R. B. Eskovitz, C. A. Richelen, R. M. Podoloff and M. H. Benjamin, p. 1, date unknown.
"A Flexible Printeed Circuit Board for Monitoring Patterns of Foot Loading," Craig A. Kirkwood, B.Sc., and Brian J. Andrews, Ph.d., ICAART 88-Montreal, pp. 488-489, date unknown.

Primary Examiner—Stephen C. Pellegrino
Assistant Examiner—Guy V. Tucker
Attorney, Agent, or Firm—Morgan & Finnegan

[57] ABSTRACT a capacitive biofeedback sensor including a polyurethane dielectric sandwiched between two wire mesh or carbon impregnated silicone rubber conductors. The sensor is placed within a patient's shoe, boot, ankle, brace, crutch, hand rip, wheelchair, etc., and provides biofeedback to help patients relearn function or prevent complications that impede function.

20 Claims, 7 Drawing Sheets

CAPACITIVE BIOFEEDBACK SENSOR WITH RESILIENT POLYURETHANE DIELECTRIC FOR REHABILITATION

BACKGROUND OF INVENTION

This invention relates to apparatus for medical and therapeutic application and, more particularly, to a sensor for providing biofeedback signals to help patients relearn various physical functions, or to prevent complications that impede these physical functions.

Frequently, it is desirable to observe the mechanical pressure applied in performing some otherwise routine physical function, not only by a patient suffering from some illness or disability, but also from a recovering patient, who is trying to regain, or at least to improve some physical function. This need to observe the mechanical pressure applied by the patient in performing a particular function also extends to patients who require braces or other orthotic apparatus, as well as to prosthetic equipment, or artificial limbs, and assist devices of which crutches, wheelchairs and the like are typical.

Unconscious or involuntary bodily processes, for example, the pressure distribution applied by the sole of a foot to the inner sole of a shoe while walking, the action of the ankle, also while walking or, the application of bodily weight to a pair of crutches and the like, if made perceptible to the senses can in many instances be modified through conscious mental control to produce a proper gait, or to develop the correct use of crutches in order to avoid impairing those nerves that control arm movement and sensation, the brachial plexus. This treatment technique, often referred to as biofeedback, is beneficial. Unfortunately, known biofeedback techniques and equipment are unsatisfactory for a number of reasons and, as a consequence are not in general use by patients either in acute care, rehabilitation or at home in spite of the need for devices of this nature. However, the need for them is compelling.

For instance, biofeedback may provide for monitoring the weight applied to a limb ("limb load monitoring"). An important example of this limb load monitoring relates to limiting the weight that is borne by the limb when recovering from leg fracture or joint replacement. Total hip replacements alone are performed 200,000 times per year in the United States and "toe-touch" or "partial" weight bearing is almost always prescribed for the recovering patient by the surgeon. Partial weight bearing continues until healing has progressed sufficiently to allow the patient to apply full weight to the recovering member safely. In almost all rehabilitation centers, however, there is no way to assure compliance with this prescribed treatment except through observation by trained personnel. Although the true cost of excessive weight bearing in these circumstances does not seem to have been systematically studied, it is nevertheless reasonable to assume that this failure to systematically control the weight borne by a recovering limb prolongs healing time, increases the duration of hospitalization and patient dependent status. Thus, it seems that a reliable apparatus for systematically monitoring the load applied to a recovering limb could significantly reduce this apparent loss in patient recovery time and the effort required of trained therapists as well as reducing inefficient use of medical facilities and attendant expense.

In addition to the need for improved rehabilitation techniques, described above, there are a number of applications of limb load monitoring to gait training. Limb load devices would help amputees to apply weight to prosthetic limbs in a symmetrical manner as a prelude to progressive ambulation. Children with cerebral palsy might be taught to walk correctly by placing weight on the heel and stop walking with an equine, or downwardly pointing ankle. In this way, inpatient rehabilitation service time could be reduced, and safe ambulation promoted.

Other potential applications include rewarding the patient for meeting other strength goals. Illustratively, developing muscular contractions without significantly shortening the muscle fiber in the hand or knee, that is, isometric grip strength and knee strength might be improved through biofeedback technique. Further, individuals with rheumatic diseases also could greatly benefit from effective limb load monitoring.

Another group of patients, suffering from disabilities that confine them either permanently or temporarily to a wheelchair also could benefit from a practical application of biofeedback to their status. Paraplegics, persons with spina bifida and others who lack feeling or sensation below the waist would benefit from a biofeedback signal, cuing them to shift their weight on the seat of the wheelchair and reduce the possibility of sacral pressure ulcers. Still another group of patients, bound to wheelchairs, are those suffering from mental deterioration and strokes. In either instance, falling from a wheelchair is an all-too-common injury for patients of this nature and some biofeedback mechanism that could lock the wheelchair brakes before rising from the wheelchair would reduce injury and promote safety awareness.

Naturally, a great deal of effort has been applied to develop apparatus that will provide a reliable, inexpensive and accurate biofeedback device. These efforts involved a number of technologies that can be categorized, generally, as capacitive, resistive, hydraulic, pneumatic and also of a general, miscellaneous character for providing an accurate measure of the pressure applied by a patient to a surface.

Capacitive transducers for biofeedback operation have inherent benefits in monitoring the loading on limbs or on other body parts. As the weight of a patient is applied to a measuring capacitor, there is a relatively linear increase of capacitance with applied weight, which permits the use of simple, low cost electrical circuits to generate a signal that is directly proportional to the applied weight. In this way, a capacitive transducer might be developed to measure the total weight that is applied to complex, irregular surfaces. In spite of this potential, capacitive transducers have been overlooked during most of the past decade in favor of resistive devices. What has been lacking, and made capacitive transducer research for this purpose unattractive has been the lack of an acceptable dielectric.

The dielectric is the insulating middle layer that is interposed between the electrically conductive plates that comprise the capacitor. Ordinarily, the dielectric properties remain constant as a force, such as that applied by a limb, compresses the dielectric and brings the conductive plates closer together thereby causing the capacitance of the sensor to increase measurably.

Many dielectrics, however, are subject to creep, which is the long term change in the dielectric thickness after initial loading. Dielectrics also are subject to hysteresis, which is the difference in compression, or capacitance, at a given load with the load increasing, and with the load decreasing. The sensitivity of the dielectric, or the ratio of capacitance in the loaded and unloaded state, per application of unit weight also is an important parameter. The speed with which the sensor achieves steady state after weight is applied, or the dynamic response of the dielectric and the resiliency of the dielectric, which is the ability of the dielectric to retain its unloaded thickness and baseline capacitance after a long duration of static or dynamic loading also are significant factors in choosing suitable dielectrics. All of these properties are a function of the dielectric material composition and structure. Ideally, for the purpose of a biofeedback sensor, a dielectric should enjoy zero hysteresis and creep with a very high resilience, sensitivity, and dynamic response.

The Krusen Limb Load Monitor is an illustrative prior art device. This device is described in Craik, R. and Wannstedt, G., *Proceedings 2nd Conf. Devices and Systems for the Disabled*, 1975, 19–24. The capacitive transducer consists of three layers of copper- Mylar ® laminate the outer two layers of which are separated from the inner layer each by a layer of "closed cell foam tape". The whole device, as shown in the paper, has the shape of an inner-sole. The characteristics of the dielectric, however, were not published. This device nevertheless fails to provide a fully satisfactory capacitive transducer because it lacks adaptability to orthotics (i.e., braces), assistive devices or wheelchairs and it is expensive.

Additionally, if conventional polyethylene foam tape is the dielectric that is used in this apparatus, the capacitive transducer also should be subject to significant hysteresis and creep, and would be unsatisfactory after repeated compression which would require frequent replacement.

An apparent improvement in the foregoing device, in which two layers of Neoprene sponge, laminated between three layers of copper foil is described in Miyazake, S., and Ishida A., *Medical and Biological Engineering and Computing*, 1984, pp. 309–316. Unfortunately, Neoprene, like polyethylene, has limited resilience to static and dynamic loading and also is unsatisfactory with repeated use.

On initial testing there was good agreement between force plate and transducer data on patients with foot shapes that were not markedly abnormal. However, higher local pressures from deformed feet caused excessive error (i.e., overestimation of weight). To reduce this error stiff plastic was built into the laminate to spread out area of force application. This modification, however, produced a device that was cumbersome, thick and stiff and which prevented the capacitive transducer from acceptable adaptation to shoes, orthotics, assist devices or wheelchairs.

A second major category of sensors for rehabilitation are resistive devices, which appear to be the most popular approach to solving the biofeedback sensor problem. In these resistive devices a change in electrical resistance is related to the force applied by the patient to effect that change.

Force Sensitive Resistors (FSR's) are marketed by Interlink Corp. They are thin (0.25 mm thick), physically flexible, inexpensive devices available in 1 cm² squares. Externally there are two adjacent Mylar ® sheets. On one Mylar sheet is a high resistance polymer or carbon film, and on the other Mylar sheet an interdigitated or interlocked pattern of open ended conductors is formed. Ruggedness appears to be good with extended use for this transducer and it may be used with simple electrical circuits.

For these reasons FSR's have been proposed for "everyday" rehabilitation pressure measurement in several applications. These include monitoring pressure under insensate feet in patients afflicted with diabetes and leprosy (M. Maalej, et. al., IEEE, 9th Conference of the Engineering in Medicine and Biology Society, 1987, pp. 1824, 1824). A finger and hand exercise device and "spot" high pressure sensor to prevent sacral pressure ulcers have also been described (Hyman, W. et. al., *RESNA*, 13th annual Conference, 1990, pp. 201, 202). It additionally has been proposed for motorized prosthesis control (Heckathorne, C., *RESNA*, 12th annual Conference, 1989, pp. 224225)

These resistive devices, however, are unsatisfactory for several reasons. Illustratively, the response of these resistive transducers is not linear but is substantially exponential. Unloaded resistance is effectively infinite, and resistance declines rapidly as weight in the range from 10 to 20 pounds is applied. Above this range, the electrical resistance approaches an asymptotic minimum value. Finally, as this applied weight exceeds 50 pounds the change in electrical resistance may be obscured by electrical background noise. In terms of noise, moreover, the device demonstrates significant hysteresis that varies from device to device and from trial to trial with the same device.

A microprocessor and, less satisfactory, an integrated circuit can be used to produce a linear response in which the electrical output is proportional to the applied pressure. To determine the weight applied to a large irregular contour, the output signals from many linearized sensors must be summed, and this use of more sensors makes accuracy less dependent on variations of contour. This solution to the problem increases the complexity of the associated electrical circuits, reduces reliability and dramatically increases current drain which decreases the battery life for portable devices. Because of battery drain alone, FSR's would be unacceptable for use in a wheelchair embodiment.

To use a minimum number of sensors, FSR's must be placed at points of maximum pressure. For instance, for limb load monitoring, sensors may be placed on the first and fifth metatarsals and the heel. Should a patient have an irregular foot contour or wear a cast, the resistive sensor placement must be customized.

Biofeedback for hand grip strength application using FSR's presents an even more serious problem, as hand size and placement are difficult to control. Thus, FSR's lack flexibility where total pressure is to be obtained over irregular or complex surfaces. In contrast, capacitive devices are not so inflexible or cause as much current drain. Indeed, FSR's and other resistive devices are best used, not in a dynamic environment between the patient and the therapeutic or prosthetic device, but in static situations in which local pressures are to be mapped and quantified over two dimensions, e.g. to identify skin areas that are at risk for breakdown and ulceration. Calculated forecasts based on resistive transducer data, may, for example, guide the prescription of custom shoes.

One such resistance device is based on the flexible force sensor developed by Polchaninoff in 1984 and described in U.S. Pat. No. 4,426,884. The electrical behavior of this sensor is similar to that of the FSR described above. Twenty of these sensors, moreover, are incorporated into the "multi-event notification system for monitoring critical pressure points on persons with diminished sensation of the feet" shown by Goforth in his 1987 U.S. Pat. No. 4,647,918. In the Goforth disclosure, resistors are placed under the heel, lateral plantar surface, metatarsal heads, and toes of the patient. The information signals from each of these resistors is transmitted to a portable microprocessor. The complexity, cost, and fragility of this apparatus make it unsatisfactory, however, for application to limb loading after orthopedic procedure or for gait training.

Tecscan Inc. (Boston, Mass.) has developed a pressure mapping system for gait analysis (Sensors, May 1991, pp. 21-25). in which 960 resistive elements are continuously sampled by a personal computer during ambulation. Graphics of excessive local pressure on the foot are displayed in real time. A similar device also has been developed by Tecscan for determining gluteal, or buttocks pressure contours. This latter system may be used for evaluating seating systems. Both of these systems, from the standpoint of a suitable biofeedback apparatus in a dynamic environment are expensive, lack durability, are fragile and complex.

Hydraulic devices easily determine total weight applied to irregular surfaces and, in this respect, are similar to capacitive devices. However, by definition these hydraulic devices measure the total weight by means of fluid pressure in a closed chamber. As a consequence, hydraulic devices tend to be large, heavy, bulky, thick or rigid. Nevertheless, hydraulic and conceptually similar pneumatic systems have been applied to limb load detection, grip strength detection, and seating pressure systems.

Two devices for providing objective and immediate limb loading data feedback are described in Sipe, U.S. Pat. No. 3,974,491 and Pfeiffer, U.S. Pat. No. 3,791,375. Both of these devices employ reservoirs below the heel and sole. Applied weight compresses these reservoirs and the force, or weight is monitored by a transducer on the patient's ankle. Apart from the need for a dedicated shoe, these transducers are difficult to put on and take off, and the height added to the shoe to accommodate these devices may impede ambulation in an individual whose walking is already impaired and possibly unsafe.

Hydraulic devices for measurement of grip strength are known as dynamometers. These devices are large and heavy and the applied force is read directly from a pressure gauge, which is difficult for the patient to read. Due to these limitations, they are not designed for use during exercise and are certainly inappropriate for the elderly or frail arthritic who would most benefit from grip strengthening.

Pneumatic devices also have been developed to measure pressures beneath bony prominences in evaluating wheelchair seats. Because these pneumatic transducers are essentially flattened, modified balloons, their size, shape and fragility make them inappropriate for permanently monitoring the weight of a patient on a wheelchair seat and they are not adaptable to the wide variety of wheelchair and wheelchair cushions now available.

Other physical phenomena have been employed, apart from the four mentioned above, to provide a measure of the physical pressure applied by a patient to some therapeutic or prosthetic device. Exemplary of this last group, the mechanical switching device, described in Gradisar, U.S. Pat. No. 3,702,999 measures limb loading. Each of two switches has two metal discs separated by an "O" ring. As weight is applied to the top disk, the "O" ring is compressed until electrical contact is established between the two discs to energize a buzzer. By adjusting a set screw on one disk, the weight at which the buzzer sounds also may be adjusted. This device is subject to mechanical problems; it is difficult to adjust the device to the "trigger" weight; and only one type of shoe (a "cast boot") may be used with this apparatus.

Other phenomena applied to biomedical force measurement include strain gauge and piezoelectric technologies. Strain gauges are made of coils of thin high-resistance wire or of metal or silicon impressions that are diffused or otherwise applied to a substrate. Because they enjoy a high level of accuracy, these transducers are good for gait research. Nevertheless, they also are fragile, expensive and consume large amounts of power. For these reasons, devices of this nature also are unsuited for the demands of daily therapeutic use. Additionally, these devices emit low power signals that require extensive amplification, a large volume, a controlled environment and are expensive.

In summary, weight bearing biofeedback apparatus and proposals that have characterized the prior art are undesirably complex, expensive, subject to failure, and lack durability. Although force sensitive resistors are promising for certain limited applications, they are substantially non-linear in electrical response and need dedicated electrical circuits that generate linear and integrated output signals that reflect the measured weight. For large, irregular surfaces an array of many FSR's must be used. This further increases the complexity and the cost for the system as well as the current drain while, at the same time decreasing durability and battery life.

Capacitive transducers, on the other hand are inherently linear and integrate the force information. Capacitive transducers further are independent of the body and transducer contours. These devices need not be customized and thus they are readily interchanged among patients.

On this basis, it seems that capacitive transducers should have the best potential for biofeedback operation except for the fact that no suitable dielectric has been identified that will permit the goals of simplicity, low cost, reliability, portability and low current drain to be achieved in a commercial device.

SUMMARY OF INVENTION

The present invention overcomes the disadvantages of the prior art. It is a capacitive transducer, consisting of an open cell polyurethane foam dielectric sandwiched between two conductors. This foam is a key feature of this invention. It is used in every embodiment. In most embodiments, the conductors are wire mesh, similar in appearance to window screen.

A second un-obvious feature of this invention is use of carbon impregnated silicone rubber (CISR) as the conductors in some embodiments. CISR is the material employed in transcutaneous electric nerve stimulation (TENS). It has high resistance to DC current. However, for measurement of capacitance it acts as a conductor. Embodiments with CISR have remarkable pliability and ruggedness.

The preferred polyurethane foam is characterized in terms of chemistry, density, firmness and morphology. Chemically, polyurethanes are formed as diisocyanates (having the general structure R—N=C=O) react with polyols (alcohols). Density is commonly referred to as pounds per cubic foot, or pcf. The preferred density range for the present invention is 5–50 pcf. Firmness, is defined as the compressive force (expressed as pounds per square inch, or psi) required to cause a 25% compression of the polyurethane foam. (A device causing a 0.2 inch/minute strain rate is used). The preferred firmness range for the instant invention is 0.1–100 psi. Morphologically, the foam is made up of a plethora of approximately spherical cells. The preferred average cell diameter is 50–200 microns. Cells are in communication through a multitude of pores (thus, "open cell"). Unimpeded air flow through the foam substance helps establish resilience. On formal testing there is a loss of 5% thickness or less on an ASTM 1667 compression set at 73 degrees F. Foams of this type are preferably manufactured by Rogers Corp., Poron Materials Division, East Woodstock, Connecticut.

The preferred polyurethane foam of this class is marketed as PPT ® (mnemonic for Personal Protective Technology), a trademark of Langer Biomedical Group. This open cell, high density, microcellular polyurethane foam has an average pore size of 100 microns, density of 20 pcf, and firmness of 10±3 psi at 25% compression. Polyurethane foams of the present invention are preferably constructed with PPT ® dielectric. Thus, in the discussion below open cell polyurethane foam is referred to as PPT ®. However, any member of the same class (with the above described components) may be used where appropriate). PPT ® (unlike other open-cell foams) has been well-known in the field of rehabilitation for several years. The conventional application is as foam padding for protective use in shoes. Although well known in the field of rehabilitation for several years, no one has thought to apply it to solve the weight bearing dilemma. However, the same features that make it a good protective foam cushion with excellent energy absorptive properties also make it the best available capacitive dielectric. These include unsurpassed resiliency to both static and dynamic loading, and linearity with compression.

PPT ® was found superior to neoprene and polyethylene foams in resiliency on extensive dynamic testing (Brodsky, et. al., *Foot and Ankle,* Vol. 9, December, 1988, pp. 111–116). PPT ® showed no loss of thickness for 10,000 cycles of compression or shear compression. (10,000 cycles corresponds to 9 hours of walking at normal cadence), whereas Neoprene showed a 5–15% loss of thickness, and polyethylene foam 15 to 50% loss of thickness. Devices made with PPT ® should thus last a very long time. Further, one expects devices made with PPT ® be far more durable than polyethylene (Krusen Monitor) or neoprene (Miyazake and Ishida device).

Furthermore, testing reveals PPT ® to have far better resiliency to static loading than polyethylene and neoprene foams. A square of PPT may be placed under a desk leg for a week and return immediately to its original shape. However, neoprene or polyethylene foams would remain permanently compressed.

The second advantage of PPT is improved linearity with compression. It is fortuitous but gratifying that this transducer is linear within narrow limits from zero to 75% compression of the dielectric. The range of linearity of pressure to compression is wider than the other two foam materials. Thus, deformed feet transferring high local areas of compression should yield equivalent capacitance change to a more spread out load. This is a clear improvement over the device described by Miyazake and Ishida.

Additionally, creep is imperceptible with greater than 75% compression for extended periods. This is in contrast to neoprene and polyethylene foams, which show significant creep at this level of compression.

Thus, this laminate is very promising as basis for a variety of weight biofeedback devices in the clinical setting. Seven specific embodiments are introduced in the following paragraphs:

A. Partial Weight Bearing Or Cast Boot Embodiment

The purpose of the cast boot embodiment is to improve compliance with toe touch or partial weight bearing orders after bone surgery on the hip or leg. This assures the shortest, safest course of post-operative rehabilitation. A cast boot is an oversized, open, canvas shoe frequently worn by such patients during daily ambulation training. A thin embodiment may fit inside a cast boot. In the preferred embodiment the conductive layer is wire screen. However, carbon impregnated silicone rubber may be used.

B. Shoe Embodiment

The shoe embodiment is intended for a patient with an insensate extremity. The well known work of Bach-Y-Rita suggests that electrically augmenting sensory feedback helps such a patient re-learn and maintain safe, functional ambulation. Conditions that lead to insensate extremities include peripheral neuropathy (e.g., from diabetes) or traumatic spinal cord injury. A secondary benefit may be reduction in foot ulceration and deformities. Many prosthetic wearers would benefit from sensory feedback, especially the many amputees with diabetes.

Physically, the embodiment resembles an inner-sole and is concealed within a shoe. This device is best employed where cosmoses and high level functioning are paramount. Use is for an indefinite period due to a chronic condition. Low cost and long life are likely to create a market for this embodiment. In the preferred embodiment the conductive layer is wire screen. However, carbon impregnated silicone rubber may be used.

C. Ankle Brace Embodiment

Children with diplegic cerebral palsy tend to ambulate with an equinus (i.e., downward pointing) ankle due to poor cerebral processing of motor information. They adopt normal heel strike only when constantly reminded (i.e., cued). This behavior persists despite use of an AFO (ankle foot orthosis, or ankle brace), specifically designed to prevent it. An embodiment is described which allows electronic cuing of heel strike. It is designed to be used with an AFO. Previous work (Seeger, B. R., Archives of Physical Medicine and Rehabilitation, 56: 237–240) suggests such a device would improve ambulation in these children. In the preferred embodiment the conductive layer is wire screen. However, carbon impregnated silicone rubber may be used.

D. Grip Strength Embodiment

Isometric strengthening (i.e., exercise of a muscle without change of its length) is preferred in treatment of arthritis and tendinitis of the hand. This is because joint and tendon movement tends to worsen inflammation. The grip strength embodiment measures grip pressure without perceptible movement of the device. This is due to the characteristics of the polyurethane dielectric in the capacitive transducer. It is designed to replace the heavy and cumbersome dynamometer that works on hydraulic pressure. The present invention is small and lightweight, and thus may be used by even a weak, frail patient without supervision. By giving continuous feedback about force applied, it will improve motivation and quality of exercise in these patients. It may also be used for strengthening and edema control in the weak hand of stroke patients, the hand that tends to be neglected (i.e., ignored) due to the cognitive effects of the stroke. Lastly, such a device could be used by the lay public for exercise of grip.

E. Axillary Crutch Embodiment

Axillary crutches are frequently used by patients that are partial weight bearing on one leg. They transmit weight through an arm and hand to the brace instead of through the leg. However, if the crutches are used incorrectly, the brachial plexus may be injured. (The brachial plexus is a bundle of nerves passing through the axilla to control arm movement and sensation). Months of pain, weakness and numbness may result from this not uncommon injury. Strain gauges normally retail for $500.00 on up, so this device is not very cost-effective. However, the present invention has a simple construction that may enable its routine use as a safety feature within axillary crutches at relatively low cost.

F. Wheelchair Embodiment

An inexpensive, durable means to detect pressure on a wheelchair seat would have many uses. Paraplegics and patients with spina bifida, insensate below the waist, would benefit from a device to cue weight shifting at regular intervals. It might reduce incidence of sacral pressure ulcers in these populations. Malament, et. al. (Archives of Physical Medicine and Rehabilitation, 56: 161–165) demonstrated such behaviors could be learned by use of biofeedback. However, bulky hydraulic devices or expensive strain gauges have been used in the past for monitoring. Other devices are based on switches, which do not allow the patient to learn progressive weight reduction during the weight shift. The wheelchair embodiment is unobtrusive, relatively inexpensive, readily adaptable to any seat design, uses only simple electronics, and monitors gradations of pressure.

Such a device could also help reduce falls due to unassisted attempts to rise out of a wheelchair on the part of patients with dementia. An unassisted attempt would activate an alarm. It is currently very important in nursing home practice to use minimal restraint (e.g., wrist or waist straps). Thus, this device could reduce falls, a common cause of morbidity in nursing homes, and at the same time minimize physical restraint.

In terms of rehabilitation, many patients immediately after stroke are impulsive and unsafe. Pressure detection could electronically cue them to lock wheelchair brakes prior to rising, and thus promote safety awareness and reduce needless injury. All these issues could be successfully addressed by a wheelchair embodiment of my invention.

G. Pressure Pad Embodiment

These consist of sets of circular, elliptical or rectangular laminates of carbon impregnated silicone rubber and PPT. They would be used for isometric strength training (i.e., other than grip strength) in the physical or occupational therapy gym. It may inspire creativity within these disciplines and be the source of further applications.

OBJECTS OF THE PRESENT INVENTION

Thus, several objects and advantages of the present invention include:

1) Flexibility, such that it may be incorporated into weight measuring shoes, cast boots, wheelchairs, devices to measure grip or pinch, or directly incorporated within orthotics.

2) Low projected cost due to simplicity of construction.

3) Unobtrusiveness (it can be made less than 0.16 cm. or ⅛ of an inch thick).

4) Durability, as the only moving part is the compressible plastic foam, which returns to its original thickness after loading after even months of continuous use.

5) Simplicity of processing. Weight is integrated over any range desired to obtain a total weight.

6) Inherently linear output.

7) Simplicity of electronic processing due to 5 and

8) Accuracy to the extent necessary in a clinical setting.

9) Ability to obtain weight applied through large, irregular surfaces as easily as through small, regular ones: That is, ability to integrate weight over area.

Because of these advantages many embodiments suggest themselves:

1) Foot weight bearing feedback
   a) after orthopedic procedures or fractures.
   b) after stroke to facilitate re-learning of weight shifting, then ambulation.
   c) facilitate paraplegic ambulation.
   d) facilitate ambulation of amputees with prosthetic limbs.

2) Upper extremity feedback, such as to provide biofeedback or grip or pinch strength.

3) Application directly within orthotics.
   a) correct tendency towards gait deviations in cerebral palsy patients.

4) Application within assist devices, such as crutches.

5) Wheelchair seat pressure feedback.
   a) electronic cuing to weight shift in spinal injured patients prone to pressure ulcers.
   b) alarm to nursing staff that patients on fall precautions have impulsively risen from the wheelchair.
   c) cue patient to lock wheelchair breaks before rising.

6) Flexible "pressure pads" with general use within the physical or occupational gym, for muscle strengthening or endurance programs.

Other objects and features of the present invention will become apparent from the following detailed description considered in connection with the accompanying drawings. It is understood, however, that the drawings are designed for purposes of illustration only, and not as a definition of the limits of the invention for which reference should be made to the appending claims.

DETAILED DESCRIPTION OF THE PREFERRED EMBODIMENTS

A. Cast Boot Bodiment

Figure 1:
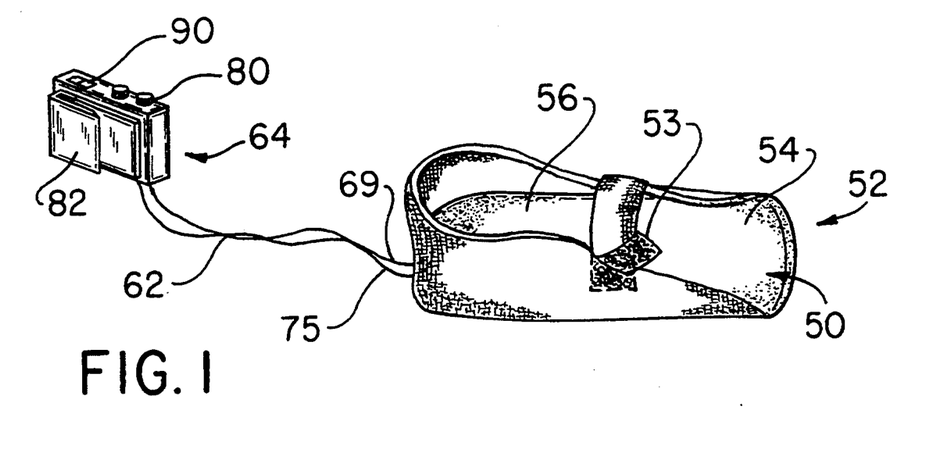
FIG. 1 is a enlarged perspective view of the cast boot embodiment within a cast boot and associated electronics module.

The cast boot embodiment is illustrated in FIGS. 1-4. FIGS. 1 affords an overview of the device. The cast boot (52) is preferably an oversized canvas shoe with an open upper surface, and fastens over the foot or cast with a Velcro ® strap (53). Also, it provides support and protection to the patient's foot.

The weight detecting element (50) sits on the upper surface of the cast boot. It is preferably very similar in shape to this platform, and not permanently glued or fastened to it. As such, it is easily installed and removed by the physical therapist. The device connects to a wire (62), then to an electronic module (64) placed on the cast boot, belt, pocket or other convenient place on the patient by means of a clip (82). Preferably, attached to the electronics module 64 is an adjustment knob (80), and an on/off switch (90). Additionally, there is preferably a piezoelectric buzzer within module 64 (not shown).

Figure 2:
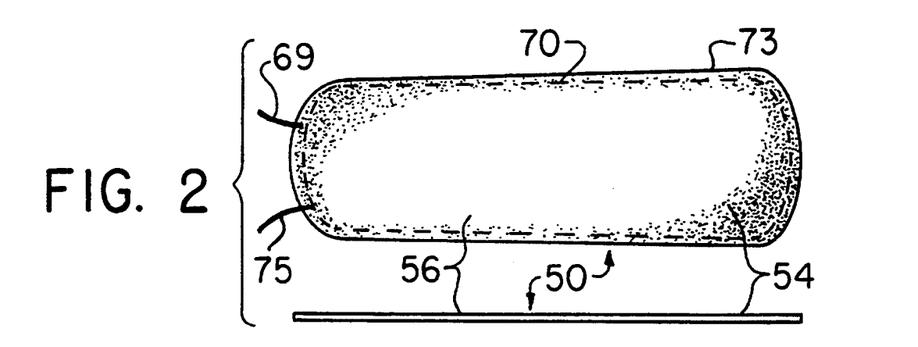
FIG. 2 is a top and side plan view of the cast boot embodiment.

The general size and shape of the device is best shown with reference to FIG. 2 which shows top and side views. Device 50 is preferably flat, planar, flexible and rectangular with rounded ends. For a 'medium' cast boot, it is preferably a maximum of 9.5 cm. wide at the forefoot (54), tapering to 8.5 cm wide at the hindfoot (56). Additionally, it is preferably 24.5 cm. long and 0.3 cm (⅛ inch) thick.

Figure 3:
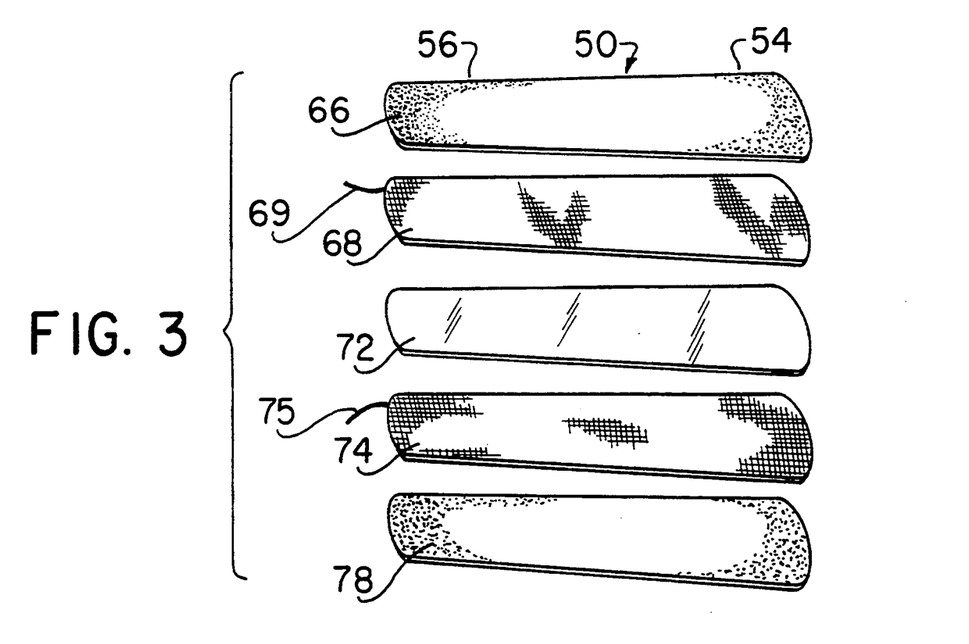
FIG. 3 is an exploded perspective view of the cast boot embodiment.

The method of fabrication is best described with reference to FIG. 3. It preferably consists of five layers. The top layer (66) is thin rubber. The next layer down (68) is steel mesh. The perimeter of this layer (69) is preferably recessed 0.7 cm from the perimeter of overall device (73). Mesh area and gauge are preferably similar to conventional window screen. Posteriorly, a wire (69) connects with the mesh, and is preferably soldered 2 cm. from one corner.

Below the mesh is a layer of polyurethane foam, as previously characterized, and preferably PPT ® polyurethane foam (72), preferably 0.16 cm. (1/16 inch) thick. Below the PPT ® is another layer of steel mesh (74), substantially identical to item 68. However, the wire (75) preferably connects 2 cm from the other rear corner of the mesh. Thus, the solder points of the wires are not directly beneath each other. Below this is the final layer (78), rubber sheet essentially identical to item 66.

All parts are preferably glued together with Contact Spray Adhesive (U.S. Pat. No. 4,401,272, 3M Company, St. Paul, Minn.). This neoprene-based product bonds well to rubber, plastic foam and metal. The five layers thus form a strong, but flexible interconnecting bond. This facilitates prolonged clinical use without loss of properties.

Figure 4:
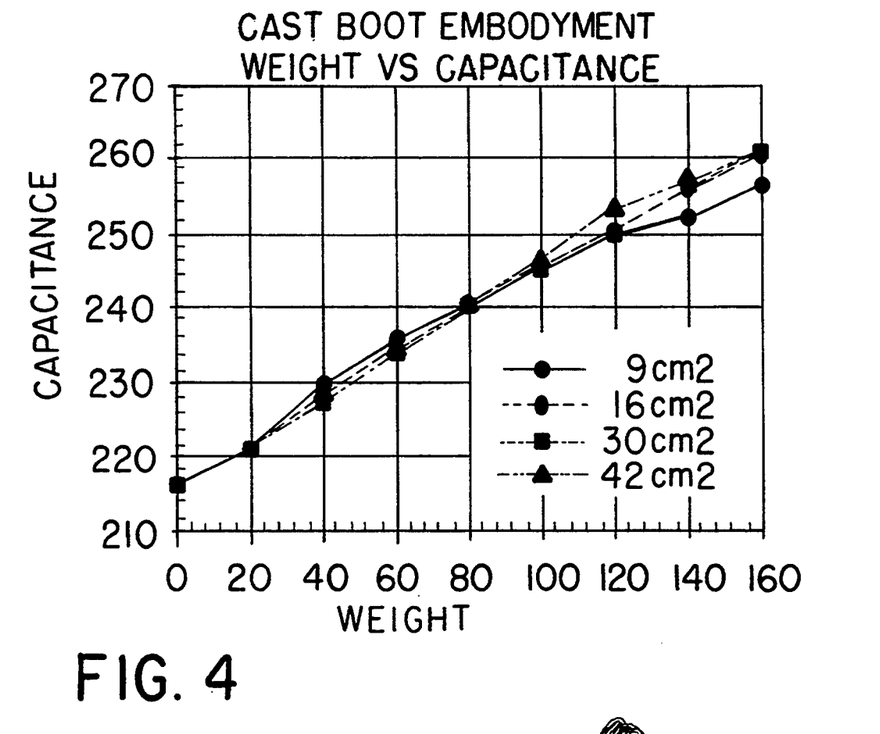
FIG. 4 is a graph of weight versus capacitance for the cast boot embodiment.

The capacitive transducer is created when the dense polyurethane foam (72) is placed between metal plates (68 and 74). As weight is applied the foam is compressed, decreasing inter-plate distance and increasing capacitance. Conversely, as the weight is removed the inter-plate distance and capacitance return to their original values. To demonstrate both stable baseline and linearity, a cast boot embodiment of the above specifications was tested for its pressure-capacitance profile. FIG. 4 is a graph describing these results. Zero to 160 lbs of weight were applied over 5 areas of weight application: 9, 16, 30.2 and 40.2 $cm^2$. (For reference, the area of the average adult great toe is about 6 $cm^2$, heel 30 $cm^2$, and forefoot 45 $cm^2$). Clearly, a high degree of linearity is demonstrated over a wide range of compression of the foam.

In a conventional manner, electronics module (64) converts capacitance linearly to voltage. Of note, top plate 68 is connected to ground to largely neutralize stray capacitance of the subject from affecting this signal. This voltage is internally compared with a trigger voltage preferably set by knob 80. This knob is set in conjunction with placing the patient's foot on a scale prior to ambulation. When weight exceeds this preset trigger a piezoelectric buzzer within the electronics module provides feedback to the patient and physical therapist. In this manner the patient is informed about toe touch, and partial or full weight bearing on the affected leg.

B. Shoe Embodiment

Figure 5:
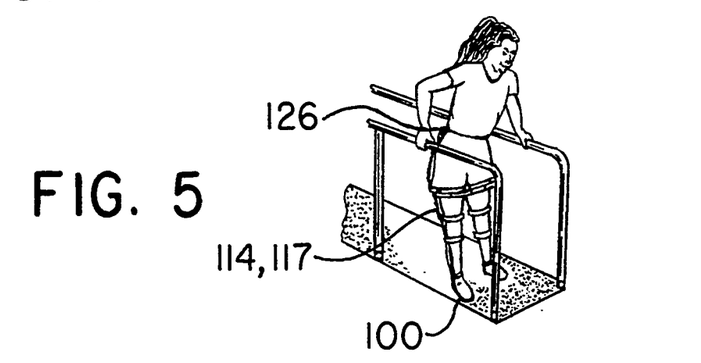
FIG. 5 is a perspective view of the shoe embodiment being used in a typical application.
Figure 6:
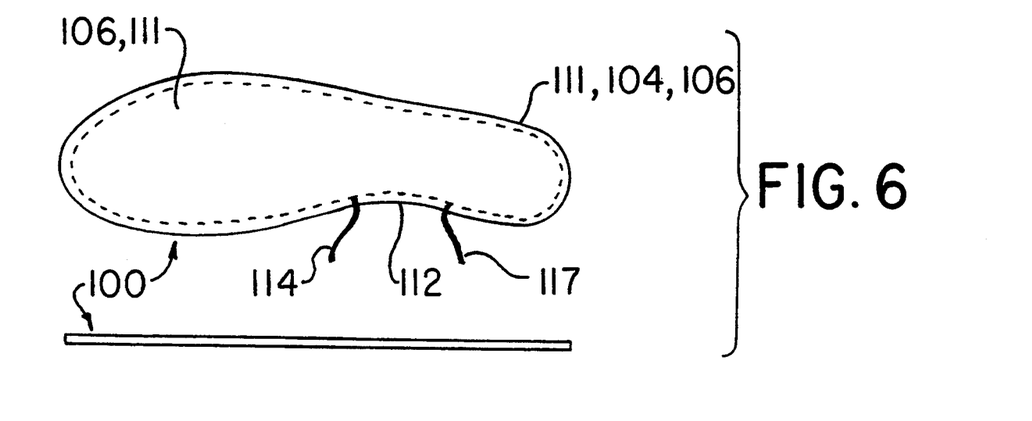
FIG. 6 is a top and side plan view of the shoe embodiment.
Figures 7, 9:
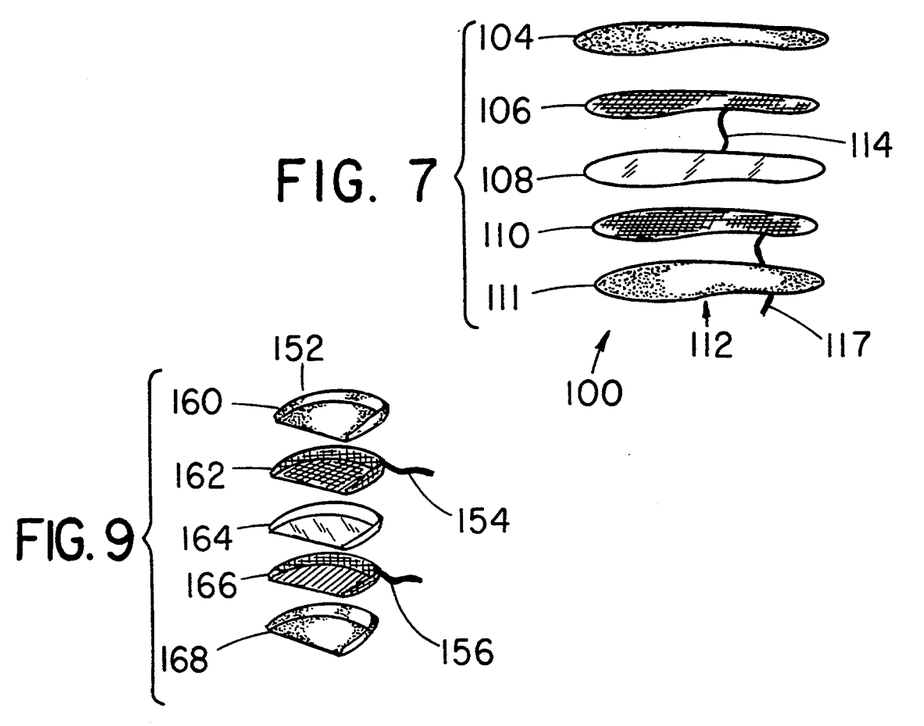
FIG. 7 is an exploded perspective view of the shoe embodiment.
FIG. 9 is an exploded perspective view of the ankle brace embodiment.

The shoe embodiment in a typical application is illustrated in FIGS. 5-7. In FIG. 5 a paraplegic is practicing reciprocal gait by weight shifting between extremities when both legs are anaesthetic. Transducer (100) is preferably beneath the inlay of an orthopedic oxford shoe on the right foot. Wires (114, 117) extend to the waist on the right side where electronic module (128) is hooked onto the belt. There is a similar configuration on the left side (not shown). The electronics module is similar in static design to the cast boot module, and has a trigger mode, and on/off switch. Inside, there is a small vibrating motor that imparts vibratory feedback to the patient. A wireless design could also be employed (not shown). This would further improve cosmoses.

The shape and thickness of the shoe embodiment is best illustrated with reference to FIG. 6. The device is preferably thin, planar, flexible and substantially flat.

The fabrication of this device is best described with reference to FIG. 7. It preferably consists of five layers. These are from top to bottom, gum rubber upper piece (104), top layer of steel mesh (106), layer of PPT (108), bottom layer of steel mesh (110), and gum rubber bottom piece (111). Steel mesh layers 106 and 110 are preferably recessed 0.7 cm inside the perimeter of the overall device. Steel mesh top plate (106) connects to a wire (114) near the front of arch (112). Similarly, steel mesh bottom plate (110) connects to a wire (117) near the rear of arch 112. These two wires connect to electronics module (128).

The calibration and operation of the shoe embodiment is similar to the cast boot embodiment. However, the feedback is preferably tactile instead of auditory. The rationale is that the audible alarm may be distracting and embarrassing for a highly functioning patient in a work or social setting. Calibration of trigger level is done by the patient by setting a threshold in conjunction with putting the foot on a scale, and varying trigger adjustment knob. Vibration intensity is all or none above this threshold. Alternatively, it can be wired to continuously increase in intensity with weight increase above a threshold. The electronic design of this device is conventional. In preliminary studies an active adult male wore this device for several hours. A stable baseline capacitance, and stable capacitance increase per unit weight increase, were noted throughout the experiment.

C. Ankle Brace Embodiment

Figure 8:
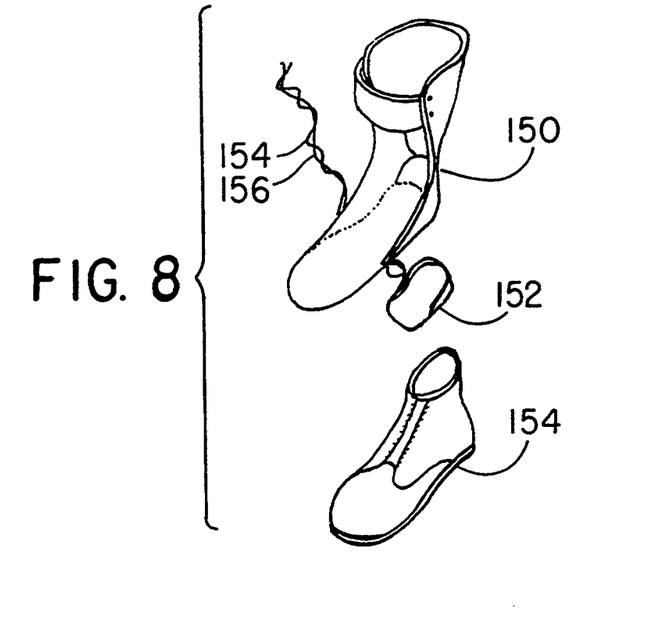
FIG. 8 is an exploded perspective view of the ankle brace embodiment.

FIGS. 8 and 9 refer to this device. FIG. 8 shows an overall perspective view. The ankle brace embodiment (152) preferably fits between the ankle foot orthosis (AFO) (150) and shoe (154). (Very often the patient with cerebral palsy has excess tone in the calf muscles. The AFO helps to control ankle movement in the face of this muscle imbalance). Wires (154, 156) go to an electronics module. This module is identical in appearance to the module 64 connected to the cast boot embodiment. Therefore, it is not specifically illustrated here. (As an alternative, transducer 152 and module 64 could be fabricated as integral parts of AFO 150).

FIG. 9 best illustrates construction of this device. As above, there are preferably five layers. They are (from top to bottom) thin rubber top piece (160), steel mesh layer (162), PPT ® polyurethane foam layer (164), second steel mesh layer (166) and rubber bottom piece (168). Wires 154 and 156 go to the electronics module. Each layer is preferably of identical thickness and composition as the cast boot embodiment.

The goal of this device is to defeat the tendency of children with cerebral palsy to "toe walk" by constant reminder to plant the heel first after the swing phase of gait. Unfortunately, toe walking frequently persists even if AFOs are worn. Prior to an exercise session the device is calibrated to elicit a sound at or near the patient's full weight. During the exercise session normal heel strike causes a transient increase in capacitance above threshold causing an audible reward signal to be emitted. However, if the foot comes down in equinus (i.e., toe strike instead of heel strike) the capacitance increase does not exceed a preset trigger and no beep is elicited. This is because after toe strike weight is never concentrated in the heel. This invention will thus assist a cerebral palsy patient learn normal heel strike during gait.

D. Grip Strength Detector Embodiment

Figure 10:
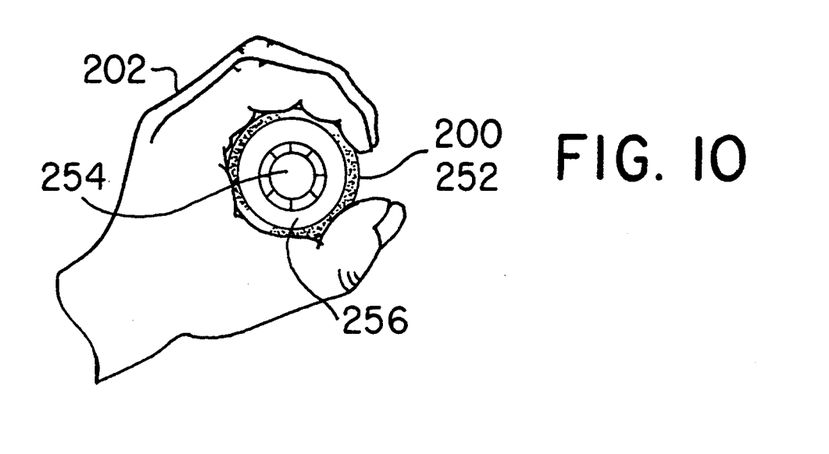
FIG. 10 is a plan view of the grip strength embodiment being used in a human hand.
Figure 11:
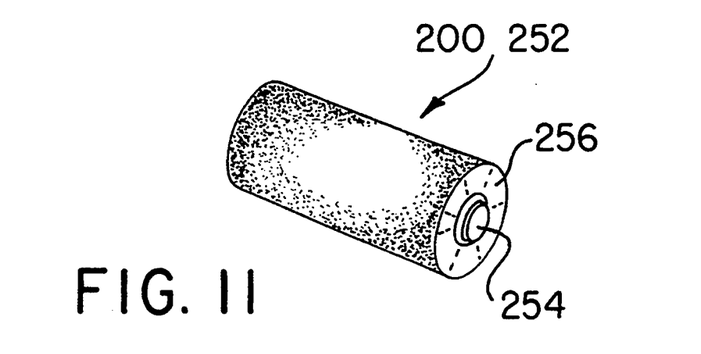
FIG. 11 is a perspective view of the grip strength embodiment outside the hand.
Figure 12:
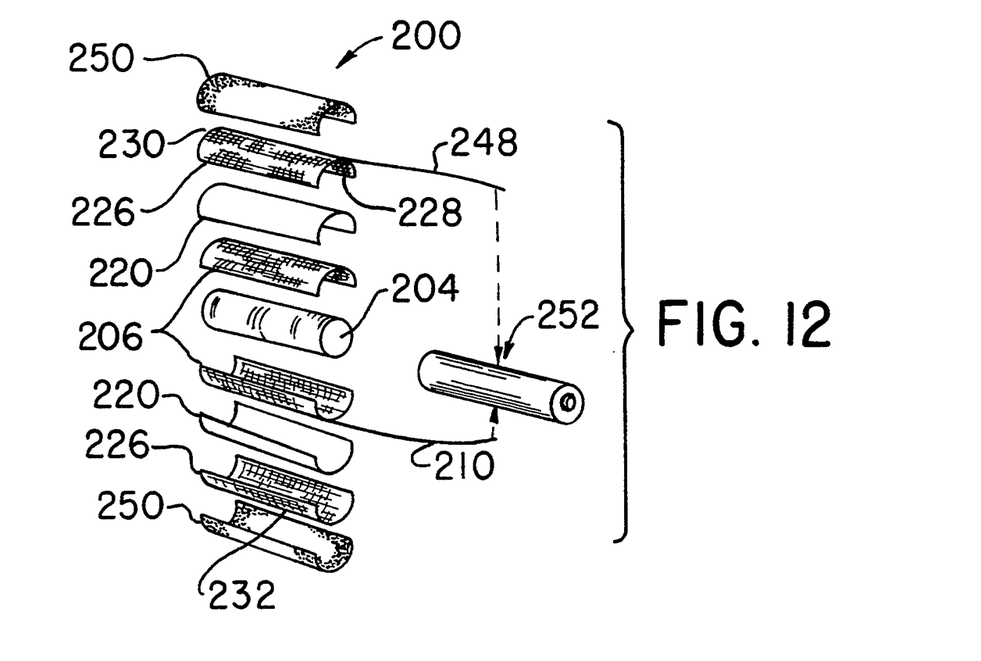
FIG. 12 is an exploded perspective view of the grip strength embodiment.

FIGS. 10-12 refer to the grip strength embodiment. FIG. 10 illustrates the isometric grip strength detector embodiment (200) in use. It is preferably cylindrical of such dimensions as to fit snugly inside the clenched adult human hand (202). An electronics module (252) is preferably incorporated inside the cylindrical transducer. Threshold strength adjustment knob (254) has a built-in on/off switch. Threshold strength can be set preferably from 0 to 60 lbs on this embodiment using preset numerical settings (256). FIG. 11 shows the general configuration of the device. It is preferably 12 cm (4.25 inches) long and 3.7 cm (1.5 inches) in diameter.

Construction of the grip strength detector embodiment 200 is best described with reference to FIG. 12 where the five layers are shown. For clarity, the four outer layers are divided into upper and lower halves and projected above and below the central cylinder. However, the cylinders are preferably continuous and concentric. Housed within device 200 is the electronics module 252.

The innermost layer (204) of embodiment 200 is preferably cellulose butyrate tubing of inner diameter of 2.54 cm (1 inch) and outer diameter of 3.17 cm (1 1/4 inch). Going outward, the next layer (206) is a cylinder of steel mesh similar to window screen. It is preferably soldered at point 208 to a wire (210) and reinforced with epoxy cement. The mesh cylinder (206) preferably fits snugly over the cellulose tubing (204), and is 144 $cm^2$ in area. The next layer (220) going outward is PPT ® polyurethane foam preferably 0.16 cm (1/16 inch) thick. Above this is a second layer of steel mesh (226) slightly larger in diameter than item 206. However, there are preferably four grooves (228,230,232,234) about 1 mm wide that extend from edge 260 to 4 mm from the other edge of the cylinder. Thus at end 260 the mesh is preferably divided into four separate sections. However, at end 262 these sections are electrically continuous. Solder connection 246 connects this layer of mesh to wire (248). Solder connection 246 is also reinforced with epoxy cement. The outermost layer (250) is preferably made up of gum rubber. Wires 210 and 248 connect to electronics module 252 as indicated by the dashes. All layers are preferably glued together with Contact Spray Adhesive (3M company). (However, other contact adhesives may be used).

To use, the patient grasps transducer 200 and applies force centripetally (i.e., toward the center) with the fingers and thumb. Grooves 228 (etc.) allow the outer mesh element 226 to contract in diameter as distance between plates 226 and 206 decreases proportional to the force applied. Secondarily, capacitance increases. In testing, capacitance increases linearly and reproducibly from a stable baseline. This baseline is 78 pF. (no force applied). Capacitance increases to 148 pF. with 70 lbs. applied.

Grip strength is calibrated in pounds prior clinical use. The pounds settings are preferably printed around the adjustment knob. The desired threshold force is set by the occupational therapist and patient uses the device as instructed. A sound emitted above a threshold serves as a reward for having achieved a given compression. (Alternatively, it could be an alarm to prevent exceeding a given compression). Experience will determine if subtle baseline shifts occur with heavy use. If so, periodic re-calibration may be required.

Although a cylindrical grasp is illustrated, there are several other important grasps. These include pinch (i.e., thumb against the lateral index finger) or ball grasp (i.e., hand grasping a ball). This invention, as a flexible laminate, may accommodate any of these shapes and provide feedback for nearly any type of grasp.

E. Axillary Crutch Device

Figure 13:
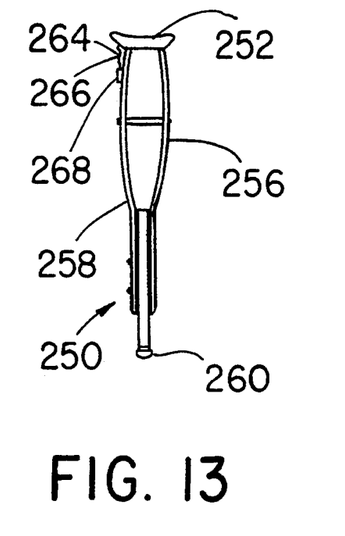
FIG. 13 is an a front elevation of an axillary crutch and axillary crutch embodiment.
Figure 14:
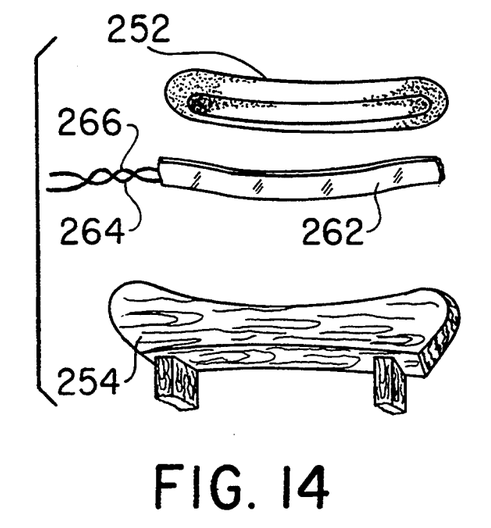
FIG. 14 is an exploded perspective view of the axillary crutch embodiment within the top of the crutch.
Figure 15:
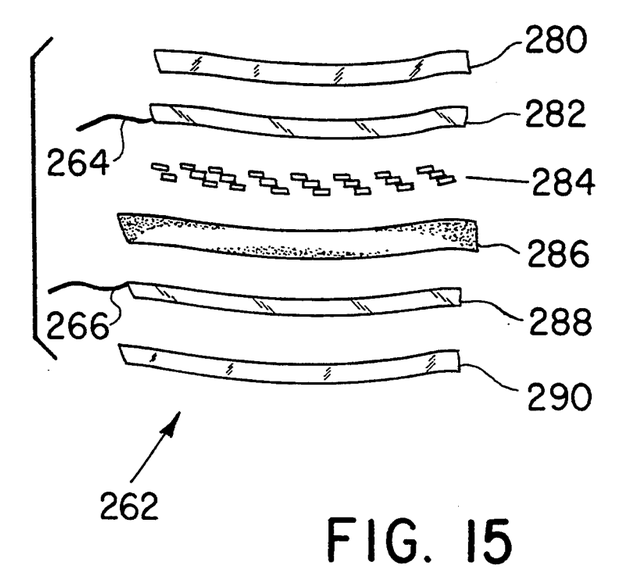
FIG. 15 is an exploded perspective view of the axillary crutch embodiment itself.

This embodiment is shown in FIGS. 13-15. An overview of the size, shape and placement of this embodiment is illustrated with reference to FIGS. 13 and 14. An axillary crutch (250) preferably has a rubber cap (252), which fits over a convex wood top-piece (254). From this, long, vertical, bowed wood members (256,258) converge on the rubber base (260). A transducer (262) is preferably interposed between rubber cap 252 and the top piece 254. The overall perimeter of transducer 262 is preferably the same as this top-piece, and it fits snugly inside the rubber cap. A set of two wires from the transducer (264, 266) go to an electronic module (268) fastened near the top of one of these two vertical wood members. In the preferred embodiment, module 268 has no external controls. Internally, there is an on-off switch, weight trigger control adjustment and piezoelectric alarm device similar to the cast boot electronics module (64).

The construction of this transducer is best described with reference to FIG. 15. There are preferably six layers from top to bottom. An uppermost layer (280) is preferably made of Orthoplast ®, a ⅛ inch thick semi-rigid plastic the shape of which may be molded at the temperature of boiling water. Below this is preferably a copper foil layer (282), of the same length and width as the Orthoplast ®. Wire 264 is soldered from foil 282 to the electronics module 268. Below this is a layer of polyurethane foam elements (284). Preferably there are 24 such rectangular pieces, about 0.95 by 0.50 cm. (0.375 by 0.2 inches), regularly spaced in a staggered arrangement. These preferably cover about 33% of the area between the adjacent layers. Below this is preferably an oversized layer of thin rubber insulation (286). Below this is copper foil (288) essentially identical to foil item 282. Wire 266 connects this layer to electronics module 268. The bottom layer is preferably Orthoplast ® (290), of very similar dimensions to the corresponding top layer 280. All layers are preferably glued together with Neoprene contact adhesive. The overhanging edges of rubber layer 286 preferably fold under the Orthoplast ® layer 290. This is so copper layers 282 and 288 will not short together.

In operation, a reference trigger weight (voltage) is set internally within the electronics module. An audible alarm sounds if the weight applied through the axilla exceeds a this reference weight. The accuracy is periodically checked by a physical therapist using an inexpensive scale, and re-adjusted if necessary.

By way of theory, the smaller area of polyurethane foam improves the sensitivity of the device. Sensitivity may be defined as the ratio of capacitance change to baseline capacitance. With one third of the area covered, sensitivity increases three times. Semi-rigid plastic members 280 and 290 are then used to more evenly transmit this weight over the set of compressible elements 284. By this method, capacitance increases linearly from a baseline of 70 pF. with 0 weight applied, to 140 pF. with 70 lbs. applied. A similar result would be obtained if a lower density of polyurethane foam were available. Then, the foam layer could cover the entire area between the plates, and eliminate the need for separate reinforcement and insulation layers.

F. Wheelchair Pressure Detector Embodiment

Figure 16:
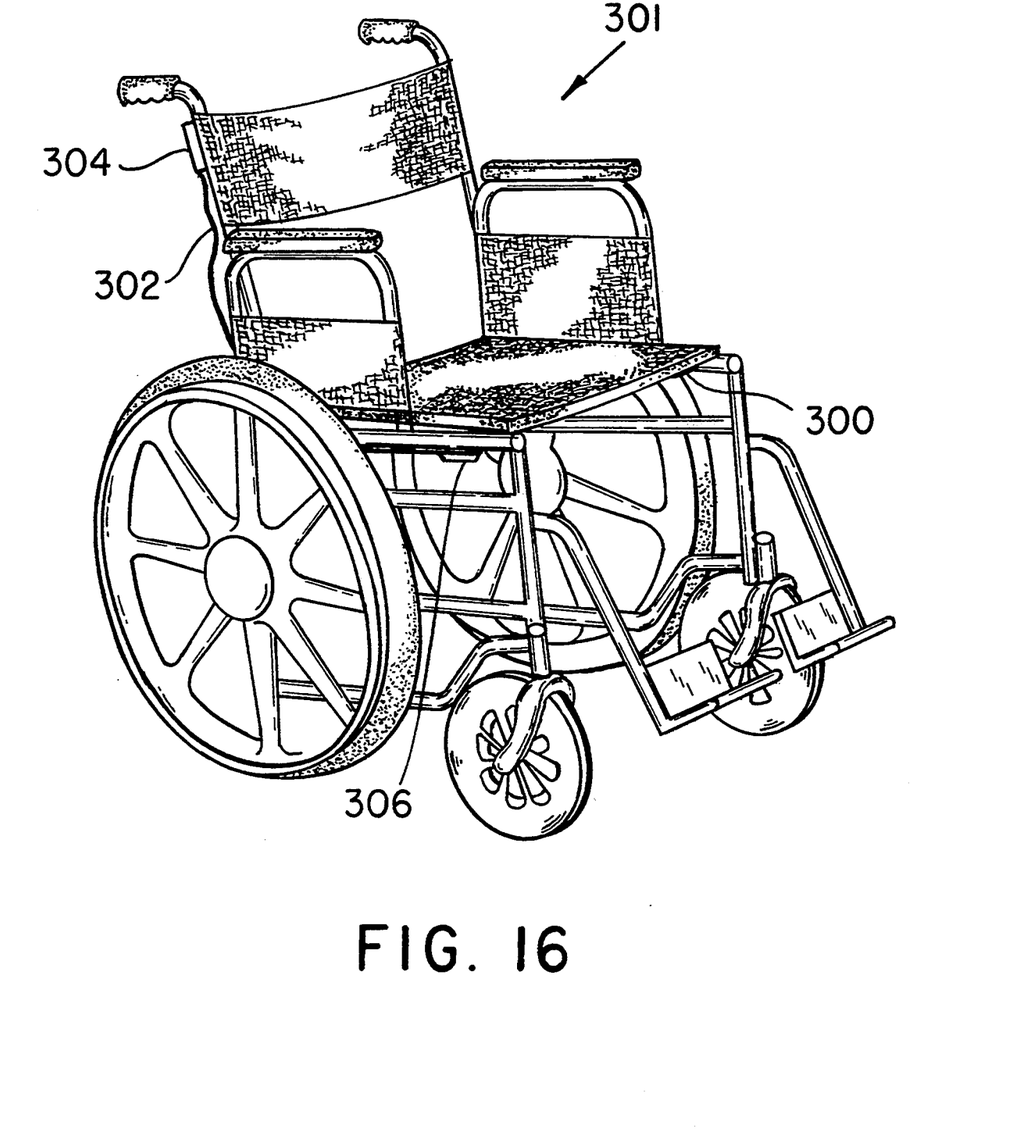
FIG. 16 is an perspective view of a wheelchair with the wheelchair embodiment within the seat.
Figure 17:
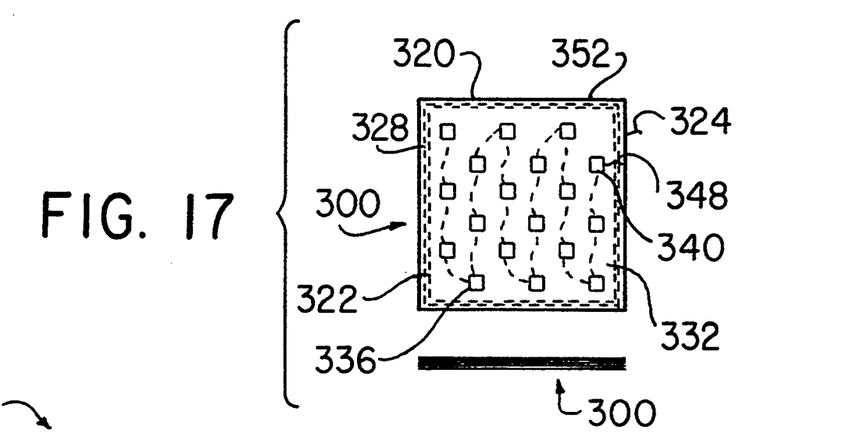
FIG. 17 is a top and side plan view of the wheelchair embodiment.
Figure 18:
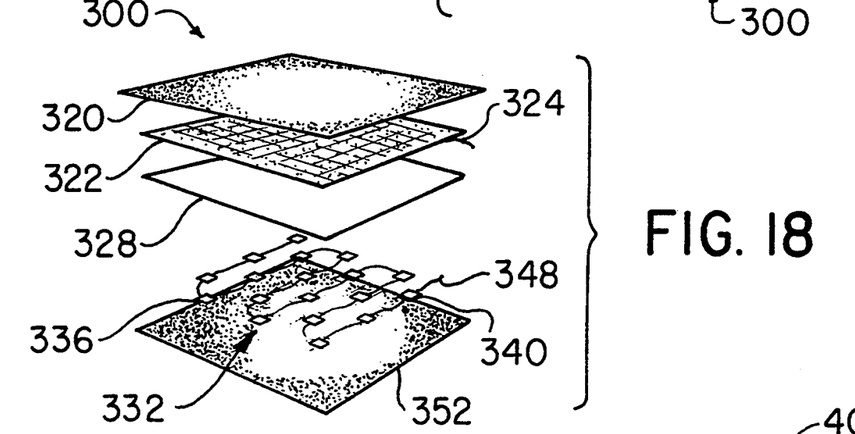
FIG. 18 is an exploded perspective view of the wheelchair embodiment.

FIGS. 16-18 refer to the wheelchair embodiment of the present invention. FIG. 16 affords an overview of this device. A pressure detector (300) is preferably placed in the sling seat of a standard wheelchair (301). This seat consists of and upper and lower vinyl member joined on the two sides. Transducer 300 fits easily between the vinyl panels that make up this seat. As it is preferably thin, flexible and smooth, it conforms to the curvature of the seat with the wheelchair folded, open or occupied, and it adds no irregularities to the seat. In other embodiments (not illustrated) the device may be placed between a sling or solid seat and special cushions, including a Jay ® and Roho ® cushion. Lead 302 connects transducer 300 to electronics module 304 located on the backrest. (Module 304 is physically equivalent to cast boot electronics module 64). In other embodiments leads may extend to toggle brake 306.

The size and shape of transducer 300 is more exactly illustrated in FIG. 17, which shows top and side views. It is preferably square, 33 cm. (14 inches) on a side and is 0.3 cm. (⅛ inch) thick. Moving inward, the dashed concentric outlines and perimeters are best presented in the exploded view, shown in FIG. 18.

The construction of transducer 300 is best illustrated in FIG. 18. As with previous embodiments, there are preferably five layers. The top layer (320) is preferably rubber sheet. Just below this is the upper layer of steel mesh (322). It is similar to window screen in appearance and is preferably 33.6 cm. (12.5 inches) on a side. It is connected to wire (324), thence to electronics module 304 (not shown on this figure). Preferably, below this is a layer of PPT ® foam (328), 0.16 cm (1/16 inch) thick, and 31 cm (13 inches) on a side. Below this is a plethora of steel mesh elements (332), preferably forming a "daisy chain" of mesh elements. The chain preferably doubles back after every 3 elements to form 6 rows of elements. Preferably, square 336 and 16 others are connected by two wires, and the end square 340 and one other, are connected by one wire, to adjacent squares. All told, 18 substantially identical squares are connected electrically in series. Representative squares 336 and 340 are preferably 2.54 cm. (1 inch) on a side. Their centers are preferably 10.2 cm (4 inches) distant from their immediate neighbors along a row or column, and 7.0 cm along a diagonal. All other squares are similarly related to their neighbors. A wire (348) connects the set 332 to the module 304. The bottom layer is preferably another piece of thin gum rubber (352). As with other embodiments, the layers are preferably glued together with Neoprene Contact adhesive.

Device 300 is a capacitive transducer that preferably works in similar manner as cast boot device 50. However, weight is applied over a much larger in area than the cast boot. Because capacitance is directly proportional to plate area, a test device with both plates full size (i.e., the size of mesh element 322) had a baseline capacitance of 800 pf. This is compared to 215 pF. for the cast boot device (50) (see FIG. 4). Sensitivity is here defined as the ratio of capacitance change to baseline capacitance. Because of the larger baseline capacitance, the 20% sensitivity of the cast boot device decreased to only 5% for the initial wheelchair prototype. By sampling weight over 18 equidistant much smaller areas sensitivity improved to 35% for the preferred embodiment. The only caveat for sampling of discrete points is that weight be relatively evenly applied over the entire surface. For the gluteal region this assumption is reasonable.

In terms of function, electronics module 64 is modified internally. Here, an increase in weight (voltage) above the trigger set by knob 80 turns off an alarm. Conversely, a decrease in voltage (weight) below the trigger turns on the alarm. This is opposite the alarm sequence of the cast boot device.

To operate, the nurse or physical therapist has the goal of being notified if a patient is rising impulsively out of the wheelchair. The trigger is thus preferably set to about one quarter the patient's weight with knob 80. The device is engaged by turning on switch 90. Thus, if the patient rises, the alarm will sound and help summoned. (In some embodiments, a delay may be built in so the patient may weight-shift without sounding the alarm).

The other two uses mentioned in the beginning of this section may be accomplished by modification of electronics only. For paraplegics, a weight-shift off the gluteal region would reset an timer circuit. If a second weight-shift did not occur with a preset interval, an alarm would sound. For the stroke patient, setting both toggle brakes would disengage the alarm circuit that would otherwise sound on standing or transferring.

Lastly, the upper plate 322 is grounded to prevent stray capacitance from affecting weight measurement.

G. Pressure Pad Embodiment

Figure 19:
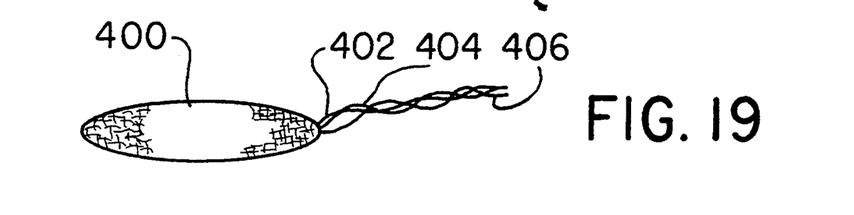
FIG. 19 is a perspective view of the pressure pad embodiment.
Figure 20:
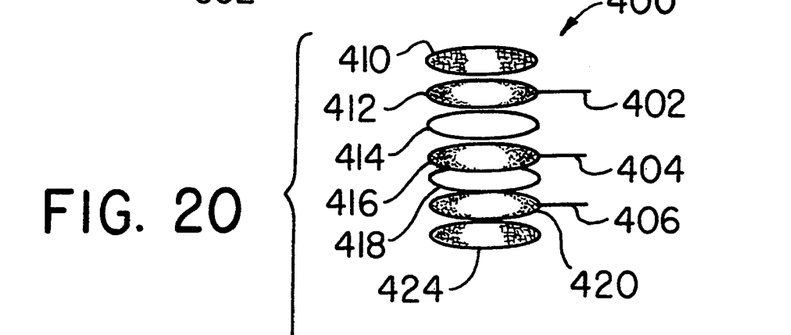
FIG. 20 is an exploded perspective view of the pressure pad embodiment.

FIGS. 19 and 20 refer to this device. FIG. 19 is an overview. The pressure pad embodiment (400) is more flexible than those discussed above by virtue of carbon impregnated silicone rubber (CISR) as the conductive layer instead of wire mesh. Preferably, the pressure pad is circular. It is preferably connected by three wires (items 402, 404, and 406) to an electronics module. This module is otherwise identical to electronics module 62 (cast boot embodiment). Therefore, it is not shown.

FIG. 20 best illustrates construction of the pressure pad embodiment 400. A cloth upper surface 410 preferably fits above a layer of carbon impregnated silicone rubber (412). The latter is preferably 0.16 cm. (1/16 inch) thick. (However, 0.08 cm. may also be employed to increase flexibility). Below this preferably is a layer of PPT ® polyurethane foam (414). Below this is preferably a central layer of carbon impregnated silicone rubber (416), and below this is another layer of PPT ® (418). Below this is the lowest layer of carbon impregnated silicone rubber (420). Below layer 420 is the bottom cloth layer 424. Layers are preferably glued with Neoprene cement, after roughening apposing surfaces with sandpaper, or other appropriate abrasive. Wires 402, 404 and 406 are preferably glued to conductive layers 412, 416 and 420 respectively, by means of a conductive silicone rubber cement. PPT ® layers 414 and 418 and cloth layers 410 and 424 are preferably of equivalent diameter and 0.5 cm greater in diameter than silicone rubber layers 412, 416 and 420.

Application of weight increases capacitance by compressing foam layers 414 and 418. This brings closer conductive layers 412, 416 and 420. Testing reveals a linear relationship between weight and capacitance. This is true for various areas of weight application, similar to that shown in FIG. 4.

In previously described embodiments there was only one capacitive layer, made up of two conductive layers with interposed dielectric foam. In those, only one surface, the layer closest to the patient, was electrically shielded. Only this side could face the patient without producing spurious readings. Those embodiments are said to be "polarized". For this embodiment there are essentially two capacitive layers in parallel. Both outer surfaces are grounded (i.e., shielded). Thus, either surface may face the patient without causing spurious readings. This embodiment is thus "non-polarized".

CISR is a suspension of small carbon particles within silicone rubber. Its conductivity is directly related to frequency; it is conductive to AC but not DC signals. Since electronics module 408 measures capacitance using AC signals, rubber layers behave as would metal conductors in this context. This sensor is therefore preferably made without metal, excluding the wires (402 404 or 406).

With respect to application, this embodiment is for general isometric strengthening (i.e., other than grip strengthening). The therapist may position the device in front of the ankle and behind an immovable surface for quadriceps strengthening, behind the ankle and in front of an immovable surface for hamstring strengthening, or between the knee and wall for gluteus medius strengthening. There may be occasions where the both surfaces are in contact with the patient, as if placed between the knees for adductor strengthening. In this case double shielding prevents spurious readings. The patient gains reward for reaching certain strength goals by auditory feedback.

In other embodiments, the device could be made a rectangular shape of various dimensions. Non-polarized pads could be used for strength and endurance training. Non-polarized rectangular pads could be made to fit various cast boot sizes, and take the place of the cast boot embodiment. Non-polarized inner-sole shaped devices could take the place of the shoe embodiment. Non-polarized circular devices could take the place of the AFO embodiment. Further, very thin (i.e., 0.8 cm. or less) conductive silicone rubber layers would make for very flexible, resilient devices between irregular surfaces.

Additional improvements could be made to the electronic module. Continuous digital display of weight in pounds is possible. This would be very helpful for weight training. Beyond this, a portable digital scale for the mass market could be made in the following way: Two rectangular or inner-sole shaped pressure pads could be positioned on a flexible plastic screen. These pads would be connected to a small electronics module with digital readout in pounds, also positioned on the screen. For a weight conscious person "always on the move", the device could be unrolled onto a hard surface such as a hotel bathroom floor and re-rolled for travel.

Accordingly, the reader will see that this invention is a capacitive transducer with wide potential application in the area of rehabilitation medicine and also the mass market for exercise or toning devices. In operation the device measures the capacitance change between two metal screens preferably separated by a open cell polyurethane foam dielectric known as PPT ® . In some embodiments, the metal screen is replaced by elastic conductive silicone rubber. As weight is applied, the foam compresses and capacitance increases.

Although the concept of the capacitive transduction is not new, this device possesses many important improved properties. These including unsurpassed resiliency and durability of the dielectric. Response is linear and reproducible. It additionally has the ability to measure weight accurately when applied over a large or small area via irregular surfaces. Construction is simple, and readily available electronics may be used with very low current drain. Small batteries may thus power these devices over a long period of time.

The materials that create these improvements have been well known in the field for some time. However, no one has thought to apply them to solve the important problem of how to measure limb loading. Therefore these improvements are not obvious.

Additionally, the prior art has so far been totally unsuccessful in meeting the need for load monitoring. Very little of the prior art is actually in use. This is true even though the potential market is huge.

This invention is broad in application. It has many specific embodiments in the areas of shoes, prosthetics, orthotics, assist devices and wheelchairs. The invention would be of interest to the physiatrist, orthopedic or plastic surgeon, physical and occupational therapist. Its wide range of potential use stems from thin size, and ability to assume different shapes.

The device is simple for both patient and practitioner to operate. Thus, this invention may overcome the natural resistance of these non-engineers to "anything electronic". This is unfortunately another important reason why the prior art involving computers has been rejected by the rehabilitation and medical community.

Having gained wide acceptance, devices based on the present invention would be medically important. They would: 1) help insure accurate fracture healing by more accurate implementation of the weight bearing prescription; 2) improve safety of re-learned ambulation of paraparetics, hemiparetics, and amputees by improving sensory awareness; 3) improve ambulation of individuals with predominantly sensory loss; 4) improve upper extremity strength and reduce pain in arthritics and stroke patients; 5) reduce pressure sores in paraplegics due to prolonged wheelchair sitting; 6) reduce the rate of falls in stroke patients due to impulsively rising out of the wheelchair; and 7) improve effectiveness of strength or endurance training.

Although the description above contains many specificities, these should not be construed as limiting the scope of the invention but as merely providing illustrations of some of the presently preferred embodiments of this invention. For instance, any of the embodiments may be made wireless. The electronic modules may be made very small using surface mount or other technologies of manufacture. Thus, complete embodiments may be incorporated within orthotics, prosthetics or assist devices. There may be other means used to provide biofeedback to the patient besides sound or vibration.

Thus, the scope of the invention should be determined by the appended claims and their legal equivalents, rather than by the examples given.

What is claimed:

1. A capacitive biofeedback sensor comprising:
    (a) a dielectric for the capacitive biofeedback sensor, said dielectric having continuous opposite sides, said dielectric having a hysteresis and creep that approach zero and having a high resilience, sensitivity and dynamic response, wherein the percent loss of dielectric thickness change is negligible when subjected to cyclic compression and shear compression tests:
    (b) two conductors, each on a respective one of said opposite dielectric sides to establish a common, fixed area therebetween, wherein one of said conductors is secured to said one opposite side of said dielectric and said other conductor is secured to said another of said sides of said dielectric;
    (c) an electrical circuit for one of said conductors and said other conductor, wherein upon compression of said dielectric, said electrical circuit detects and measures a linear response in the capacitance through the change in separation between said conductors and compares said capacitance with a preset value set within said electrical circuit; and
    (d) feedback for imparting information to a user according to the relation between said capacitance and said preset value.

2. A biofeedback sensor as recited in claim 1, wherein said electrical circuit converts said capacitance to a voltage, wherein said voltage is compared with a preset voltage within said electrical circuit.

3. A biofeedback sensor as recited in claim 1, further comprising:
    (a) an upper insulator and a lower insulator, wherein said upper insulator is secured to said one conductor and said lower insulator is secured to said other conductor.

4. A biofeedback sensor as recited in claim 3, wherein said insulator comprises a rubber material.

5. A biofeedback sensor as recited in claim 3, wherein said dielectric, said conductors, and said upper and lower insulators are glued together.

6. A biofeedback sensor as recited in claim 1, wherein said feedback notifies said user that said capacitance between said upper and lower conductors is under said preset value.

7. A biofeedback sensor as recited in claim 1, wherein said dielectric and said conductors are glued together.

8. A biofeedback sensor as recited in claim 1, wherein said electrical circuit further comprises an adjustable knob, wherein said preset value may be adjusted.

9. A biofeedback sensor as recited in claim 1, wherein said conductors comprise a metal mesh material.

10. A biofeedback sensor as recited in claim 1, wherein said conductors comprise carbon impregnated silicone rubber.

11. A biofeedback sensor as recited in claim 1, further comprising:
    (a) a buzzer, wherein said buzzer emits auditory tones according to the relation between said capacitance and said preset value, thereby imparting auditory feedback to a user.

12. A biofeedback sensor as recited in claim 1, wherein said electrical circuit includes a delay, wherein said feedback to said user is displayed by a predetermined length of time.

13. A biofeedback sensor as recited in claim 1, further comprising:
    (a) vibratory apparatus, wherein said vibratory apparatus vibrates according to the relation between said capacitance and said preset value, thereby imparting vibratory feedback to a user.

14. A biofeedback sensor as recited in claim 13, wherein said vibratory apparatus alters vibration intensity, thereby imparting vibratory feedback to a user.

15. A biofeedback sensor according to claim 1 wherein said dielectric further comprises a polyurethane foam.

16. A biofeedback sensor according to claim 15 wherein said dielectric further comprises a density of 5 to 50 pounds per cubic foot, a firmness range of 0.1 to 100 pounds per square inch, a foam cell diameter range of 50 to 200 microns and a loss of thickness of 5% or less on an American Society for Testing Materials Compression set at 73° F.

17. A biofeedback sensor according to claim 15 wherein said dielectric further comprises an average pore size of 100 microns, a density of 20 pounds per cubic foot and a firmness of 10±3 pounds per square inch at 25% compression.

18. A capacitive foot sensor feedback device, comprising:
(a) a shoe having an open upper surface;
(b) a strap, wherein said strap fastens over said open upper surface of said shoe;
(c) a dielectric for the capacitive foot sensory feedback device, said dielectric having two continuous sides, said dielectric having a hysteresis and creep that approach zero and having a high resilience, sensitivity and dynamic response, wherein the percent of loss of dielectric thickness change is negligible when subjected to cyclic compression and shear compression tests;
(d) two conductors, each on a respective one of said opposite dielectric sides to establish a common, fixed area therebetween, wherein one of said conductors is secured to said one opposite side of said dielectric, and said other conductor is secured to another of said sides of said dielectric;
wherein said dielectric and said conductors are placed within said shoe;
(e) an electrical circuit for one of said conductors and said other conductor, wherein upon compression of said dielectric, said electrical circuit detects and measures a linear response in the capacitance through the change in separation between said conductors and compares said capacitance with a preset value set within said electrical circuit; and
(f) feedback for imparting information to a user according to the relation between said capacitance and said preset value.

19. A foot sensory feedback device as recited in claim 18, further comprising:
(a) a buzzer, wherein said buzzer emits auditory tones according to the relation between said capacitance and said preset value, thereby imparting auditory feedback to a user.

20. A capacitive sensory feedback device comprising:
(a) an ankle brace;
(b) a dielectric for the capacitive sensory feedback device, said dielectric having two continuous sides, said dielectric having a hysteresis and creep that approach zero and having a high resilience, sensitivity and dynamic response wherein the percent of loss of dielectric thickness change is negligible when subjected to cyclic compression and shear compression tests; and
(c) two conductors, each on a respective one of said opposite dielectric sides to establish a common, fixed area therebetween, wherein one of said conductors is secured to said one opposite side of said dielectric and said other conductor is secured to another of said sides of said dielectric to produce a linear change in capacitance through the change in operation between said conductors to provide the sensory feedback;
wherein said ankle brace is placed atop said dielectric and said conductors;
(d) an electric circuit for one of said conductors and said other conductor, wherein upon compression of said dielectric, said electrical circuit detects and measures a linear response in the capacitance through the change in separation between said conductors and compares the capacitance with a preset value set within said electrical circuit; and
(e) feedback for imparting information to a user accounting to the relation between said capacitance and said preset value.

* * * * *